United States Patent [19]

Dewar et al.

[11] Patent Number: 5,043,266

[45] Date of Patent: Aug. 27, 1991

[54] ORTHO- AND PARA-IMIDAZOLYL AND BENZIMIDAZOLYL SUBSTITUTED PHENOL AS ENHANCERS FOR DIAGNOSTIC CHEMILUMINESCENT ASSAYS

[75] Inventors: Margaret H. Dewar, Shotts, Scotland; Robert S. Davidson, Leicester, England

[73] Assignee: National Research Development Corporation, London, England

[21] Appl. No.: 200,456

[22] Filed: May 31, 1988

[30] Foreign Application Priority Data

Jun. 15, 1987 [GB] United Kingdom ................ 8713951

[51] Int. Cl.$^5$ .......................... C12Q 1/00; C12Q 1/28; C09K 3/00
[52] U.S. Cl. ........................ 435/7.9; 435/28; 435/810; 435/968; 435/975; 252/700
[58] Field of Search ............... 435/28, 7, 810; 252/700; 436/66

[56] References Cited

U.S. PATENT DOCUMENTS 4,729,950 3/1988 Kricka et al. .................... 435/28
4,853,327 8/1989 Dattagupta .................... 435/6

FOREIGN PATENT DOCUMENTS 219352A 4/1987 European Pat. Off. .

OTHER PUBLICATIONS

Thorpe, G. H. et al., *Clin. Chem.*, 31(8):1335–1341, 1985.
I. Fridovich et al., J. Biol. Chem. 238, 3921–3927 (1963).
W. Straus, J. Histochem. Cytochem. 30, 491–493 (1982).
T. P. Whitehead et al., Clinical Chemistry 25, 1531–1546 (1979).

*Primary Examiner*—Esther L. Kepplinger
*Assistant Examiner*—Jacintha M. Stall
*Attorney, Agent, or Firm*—Nixon & Vanderhye

[57] ABSTRACT

Light obtained from the reaction between a dihydrophthalazinedione such as luminol or isoluminol, an oxidant such as hydrogen peroxide, and a peroxidase enzyme is enhanced by addition of an ortho- or para- imidazolyl- or benzimidazolylphenol.

The effect has particular application to diagnostic assays.

16 Claims, No Drawings

ORTHO- AND PARA-IMIDAZOLYL AND BENZIMIDAZOLYL SUBSTITUTED PHENOL AS ENHANCERS FOR DIAGNOSTIC CHEMILUMINESCENT ASSAYS

BACKGROUND OF THE INVENTION

1. Field of the Invention

The present invention relates to an enhanced chemiluminescent reaction especially for use in a diagnostic assay, particularly immunoassay, and to a diagnostic kit for use in the assay. A chemiluminescent reaction is a chemical reaction which results in the emission of light. The luminescent emission is generally of sufficient duration to enable the light emitted to be detected or measured, and thereby to allow the detection or quantification of an analyte. The chemiluminescent reaction with which this invention is concerned is that between a 2,3-dihydro-1,4-phthalazinedione (DPD), especially luminol, with an oxidant, especially hydrogen peroxide, and a peroxidase enzyme, especially horseradish peroxidase, which catalyses the oxidation of the DPD by the oxidant. The oxidation is accompanied by emission of light.

2. Description of the Prior Art

Luminescent assays making use of the above-mentioned peroxidase-catalysed oxidation of a DPD include three major types. a. Assays wherein horseradish peroxidase is conjugated to a ligand in order to label it and a luminescent reaction is used to detect or quantitate the label. This category includes peroxidase ELISAs. b. Assays wherein luminescent reactions are used to determine free oxidant, peroxidase or luminol. An example of this type of assay is the determination of antibody-linked glucose oxidase by reacting the enzyme/antibody reagent with glucose to form hydrogen peroxide and then measuring the amount of hydrogen peroxide produced by adding luminol and a peroxidase catalyst under controlled conditions to initiate a luminescent reaction. c. Assays wherein a chemiluminescent compound is used directly to label ligands such as proteins, hormones, haptens, steroids, nucleic acids, metabolites, antigens and/or antibodies. The chemiluminescent DPD such as luminol or isoluminol is normally conjugated to a ligand. Chemiluminescence can be detected by adding peroxidase and an oxidant to the reacted conjugate.

A review of luminescent assays has been published by T. P. Whitehead et al., Clinical Chemistry 25, 1531-1546 (1979).

The sensitivity of the peroxidase-catalysed chemiluminescent oxidation of DPDs can be enhanced by including in the reagents an enhancer, namely a 6-hydroxybenzothiazole (European Patent 87959B), a phenol selected from a narrowly defined class (European Patent 116454B or U.S. Pat. No. 4,598,044) or an aromatic amine selected from a narrowly defined class (UK Patent Application 2162946A or U.S. Pat. No. 4,729,950). These patents and the patent application are owned by National Research Development Corporation. European Patent Application Publication No. 219352A (Minnesota Mining and Mfg. Co.) describes various aromatic amines, including some of those previously mentioned in UK Application 2162946A, as enhancers. The best of all these enhancers are believed to be certain of the narrowly defined phenol compounds. When the phenol enhancer patent applications were originally filed, the main claim defined the phenolic compounds by a general formula and by the qualification that they must act as enhancers. However, some compounds within the general formula did not confer significant enhancement. The general formula was accordingly replaced in the granted patents by a narrower definition based fairly closely on 26 named phenolic compounds found to be enhancers. The preferred enhancer is para-iodophenol (PIP). Three others gave significantly better enhancement than the rest. The phenolic enhancers all give a high signal (light output) and a low signal: background ratio (ratio of light output in the presence and absence of peroxidase enzyme), but their characteristics differ in detail. Accordingly, it is an object of the invention to extend the range of effective enhancers. This is a difficult task because no theory or mechanism has been published to explain how one should attempt to select candidate compounds to try as enhancers. It appears that para-substitution by a substituent which is not strongly electron-withdrawing is favoured, but this generalisation is of limited value, leaving thousands of compounds from which to choose.

Additional prior art is referred to below in a separate section following the "Summary of the Invention" without which its context would be unclear.

SUMMARY OF THE INVENTION

It has now been found that an imidazolyl or benzimidazolyl substituent in the ortho and/or para position of the phenol molecule, especially in the para-position, provides an effective enhancer of chemiluminescence in a reaction between a dihydrophthalazinedione (DPD), a peroxidase enzyme catalyst and an oxidant.

While the invention is applicable in principle to the enhancement of the light output from any chemiluminescent reaction involving the above-stated reaction partners, for any purpose, it is primarily of interest in connection with luminescent or luminometric assay (these terms denoting respectively a method of detection and of quantitation). For assay purposes it becomes relevant that the enhancer not only increases light output from the reaction, but also acts to enhance the sensitivity of the assay. Typically, the assay is carried out so that the light output is relatable to the amount of peroxidase employed, the peroxidase then being the substance directly determined. The ratio of light output when peroxidase is present in the sample to light output when it is absent becomes important in assuring the sensitivity of the assay. This is conveniently termed a "signal to background" ratio.

It will be appreciated that although the invention is usable to determine the presence or amount of any one of the four above-stated reaction partners, such a reaction partner is not necessarily itself the substance to be assayed. Thus the oxidant can be produced as a result of an earlier reaction or cascade of earlier reactions carried out on a sample. The peroxidase or the luminol can be in the form of a conjugate to, say, an antibody which is used in an immunoassay to determine an antigen. The invention is accordingly applicable to any method of diagnostic assay of a substance, the presence or amount of which is relatable to the presence or amount of a reaction partner selected from the group consisting of a DPD, a peroxidase enzyme an oxidant and an enhancer which together are reactable in a chemiluminescent reaction and wherein the reaction is carried out, the light output is detected or measured and thence the presence or amount of the substance to be assayed is related to the light output.

The invention also includes a kit for use in the assay comprising the DPD, the peroxidase and the enhancer. The oxidant could be supplied separately or included in the kit.

ADDITIONAL DESCRIPTION OF PRIOR ART

I. Fridovich, J. Biol. Chem. 238, 3921–3927 (1963), has found that the oxidation of o-dianisidine by hydrogen peroxide and HRP is enhanced by ammonia, pyridine or imidazole. W. Straus, Journal of Histochemistry and Cytochemistry, 30, 491–493 (1982) also reported that imidazole enhanced the above reaction and that of diaminobenzidine.

DESCRIPTION OF THE PREFERRED EMBODIMENTS

The preferred enhancer is p-imidazol-l-yl-phenol of formula:

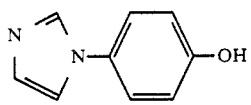

This compound is commercially available. Other enhancers of the invention include o- and p- benzimidazol-2-yl phenol of formula:

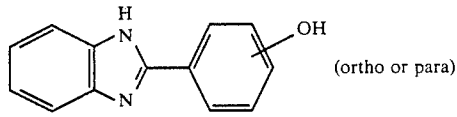

(ortho or para)

Para-imidazol-l-yl-phenol is an excellent enhancer of chemiluminescence, particularly when luminol is used as the DPD luminophore. In many circumstances it is nearly as effective as para-iodophenol, the preferred enhancer of the prior art.

The best results are obtained at higher pH. Preferably the pH is in the range 7.5 to 9 at the time of mixing all the reagents.

Any chemiluminescent DPD can be used in the invention, that is to say any DPD which is oxidisable in the presence of a peroxidase catalyst by an added oxidant to give chemiluminescence can be used. Examples are luminol, isoluminol, ABEI and AHEI, and 7-dimethylaminonaphthalene-1,2-dicarboxylic acid hydrazide, of which luminol is normally preferred. The DPD can be free or conjugated to a ligand to provide a direct label. Such luminophore-labelled assays are known in the art.

The oxidant can be any added substance (not oxygen itself) of which hydrogen peroxide is usual, but a perborate, such as the sodium salt, is an alternative.

The peroxidase enzyme will normally be HRP and of a grade appropriate to use in luminescent assays. It can be free or conjugated to a ligand. When a DPD-labelling assay is used the peroxidase is conveniently microperoxidase.

The concentrations of the reaction partners of the chemiluminescent reaction will depend on the nature of the assay being carried out and particularly on which of them is being assayed. Generally stated, the light output is greater, the greater the concentration of DPD. Thus, when peroxidase or oxidant is being assayed the use of excess DPD is recommended. Generally stated, the DPD concentration is desirably from 0.5 micromole to 200 millimoles per liter, preferably 0.5 to 100 micromoles/liter. The concentration of oxidant affects the light intensity, a high concentration of the order of millimoles/liter producing a high initial intensity decreasing rapidly with time. A lower concentration would give a lower initial output of light, but a less rapid decrease in the signal. Generally stated, the oxidant concentration is desirably in the range 0.5 micromoles to 300 millimoles/liter, preferably 10 to 200 millimoles/liter. In the Examples herein the concentrations of oxidant used were low, viz. 0.9, 1.8 and 0.6 micromole/liter in Examples 1–3.

The concentration of peroxidase is of interest if peroxidase is not the reaction partner being assayed. Excess peroxidase does not normally have a marked effect on light intensity, the peroxidase being a catalyst which is recycled. Where luminol or the oxidant is being assayed, therefore, the peroxidase need only be present in a modest concentration, such as 0.01 microgram to 5000 mg/liter, preferably not more than 50 mg./liter, but depending on the activity of the peroxidase per gram.

The concentration of the enhancer will usually be in the range 1 micromole to 4 moles/liter, preferably 10 micromoles to 100 millimoles. It is believed that the enhancer or a species or derivative thereof competes with the DPD in the reaction and it is therefore desirable to use a considerable excess of enhancer relative to the DPD, preferably between 2 and 20 times the molar concentration of the DPD.

In brief, all conditions and features of the chemiluminescent reactions, the reaction partners thereof, applications of the assay and so on (except where inconsistent with the above description) are as set forth in European Patent 116454B, the disclosure of which is herein incorporated by reference.

The following Examples illustrate the invention. The para-imidazol-l-ylphenol (IMP) used was freshly prepared.

EXAMPLE 1

This Example shows that para-imidazol-l-ylphenol (IMP) enhances a chemiluminescent reaction between luminol (LU), horseradish (HRP) conjugate and $H_2O_2$, giving a high signal: background ratio. IMP is compared with para-iodophenol (PIP).

A horseradish peroxidase conjugate, Anti-AFP-HRP supplied by Dr. G. H. G. Thorpe, Dept of Clinical Chemistry, University of Birmingham, England, was made into a stock solution, (1 mg/ml, pH 8.5, 0.1M Tris buffer). This was diluted 1:5000 in doubly distilled water, 10 $\mu$l of which was removed and added to 50 $\mu$l of sodium luminol solution (0.05 mg/ml Tris buffer, 0.1M, pH 8.5) and 300 $\mu$l of Tris buffer (pH 8.5, 0.1M). A solution of the enhancer (E), i.e. IMP or PIP, (25 $\mu$l, various concentrations of enhancer in DMSO: (a) 5 mg/ml; (b) 1 mg/ml; (c) 0.5 mg/ml) was added just before the injection of oxidant (50 $\mu$l of 6.2 $\mu$l of 30% v/v $H_2O_2$ dissolved in 10 ml $H_2O$). IMP was obtained from Sigma Chemical Company Ltd., Poole, Dorset, England. PIP was kindly supplied by Dr. G. H. G. Thorpe. The light emitted was measured by a photomultiplier at various times (in minutes) from the time of adding the $H_2O_2$. Each value represents total light output obtained by integration over a period of one minute preceding the time shown.

In comparative experiments the enhancer, the HRP or the LU were variously omitted. Table 1 shows the results. Looking first at set (a), comparison of the first and second columns, i.e. of the signal (light output) with the enhancer present and absent shows that IMP, like PIP, was a very effective enhancer. Comparison of the first and third columns shows that the "blank" or background, i.e. the light output when no HRP conjugate is present, gives a very low signal. Turning to set (b), where the concentration of enhancer has been reduced, IMP gave an even stronger signal (first column) with a diminished background (third column). The second column of set (b) illustrates the background obtained in an alternative assay reaction, in which the luminol is used as the label (instead of the more usual HRP label). Comparison of the first and second columns of set (b) shows the high signal: background ratio using luminol as the label. (Although the luminol is free, rather than conjugated, it is well accepted that free luminol validly mimics conjugated luminol in tests of luminol label assays). Set (c) shows that good results are obtained at even higher dilution of the IMP enhancer.

known as aminobutylethylisoluminol (ABEI). The enhancer concentration was 5 mg./ml. DMSO. IMP is compared with PIP.

The results are shown in Table 2, from which it will be seen that IMP is not as good as PIP with these luminophores, but still a very effective enhancer. The background runs, whether without HRP or without luminol, again gave very acceptable low light output.

EXAMPLE 3

The procedure of Example 1 was repeated except for an alteration of pH and some dilution of reagent concentrations, by adding 500 $\mu$l of each of three different buffers in place of the 300 $\mu$l of Tris pH 8.5 buffer used in Example 1. The buffers used were (a) sodium citrate (pH 4) which imparted a pH of 6.5 to the total mixture of reagents, (b) sodium phosphate (pH 7), imparting pH 8.1 to the mixture and (c) Tris (pH 9), imparting pH 8.8 to the mixture. The enhancer concentration was 5 mg./ml DMSO, IMP was compared with PIP.

From the results shown in Table 3 it will be seen that a better signal was obtained at the highest pH. IMP was

TABLE 1

| | Light output, mV/second, integrated over the preceding one minute | | | | | | | |
|---|---|---|---|---|---|---|---|---|
| | (a) 5 mg enhancer/ml | | | (b) 1 mg enhancer/ml | | | (c) 0.5 mg enhancer/ml | |
| Time (mins.) | Signal with enhancer | Signal without enhancer | Background with enhancer without HRP | Signal with enhancer | Background with enhancer without LU | Background with enhancer without HRP | Signal with enhancer | Background with enhancer without HRP |
| | IMP | | | | | | | |
| 1. | 443,996 | 102 | 540 | >600,000* | 1969 | 309 | 471,465 | 586 |
| 2. | 599,993 | 0 | 542 | >600,000* | 2940 | 301 | 599,992 | 586 |
| 5. | 537,904 | 0 | 550$^e$ | >600,000* | 1662 | 292 | 599,992 | 576$^e$ |
| | PIP | | | | | | | |
| 1. | 544,636 | 102 | 149 | | | | | |
| 2. | 599,993 | 0 | 133 | | | | | |
| 5. | 392,557 | 0 | 122 | | | | | |

*exceeded the photomultiplier capacity.
$^e$estimated by interpolation between readings.

EXAMPLE 2

The procedure of Example 1 was repeated, replacing luminol by isoluminol (IL) or 6-(N-4-aminobutyl-N-ethyl)amino-2,3-dihydrophthalazine-1,4-dione, also generally not as good as PIP but still gives a very acceptable signal.

Background runs with IMP enhancer but without luminol (not shown in Table 3) gave zero signal.

TABLE 2

| | Light output, mV/second, integrated over the preceding one minute | | | | | | | |
|---|---|---|---|---|---|---|---|---|
| | (a) Luminophore = isoluminol | | | | (b) Luminophore = ABEI | | | |
| Time (mins.) | Signal with enhancer | Signal without enhancer | Background with enhancer without luminophore | Background with enhancer without HRP | Signal with enhancer | Signal without enhancer | Background with enhancer without luminophore | Background with enhancer without HRP |
| | IMP | | | | | | | |
| 1. | 6,509 | 0 | 78 | 147 | 3,323 | 0 | 54 | 108 |
| 2. | 12,786 | | | | 7,500$^e$ | | | |
| 5. | 15,891 | | | | 8,795 | | | |
| | PIP | | | | | | | |
| 1. | 41,167 | 250 | 0 | 0 | 19,675 | 126 | 1.6 | 0.3 |
| 2. | 43,010 | | | | 22,799 | | | |
| 5. | 30,843 | | | | 15,200$^e$ | | | |

TABLE 3

| | Light output, mV/second, integrated over the preceding one minute | | | | | | | | |
|---|---|---|---|---|---|---|---|---|---|
| | pH 6.5 | | | pH 8.1 | | | pH 8.8 | | |
| Time (mins.) | Signal with enhancer | Signal without enhancer | Background with enhancer without HRP | Signal with enhancer | Signal without enhancer | Background with enhancer without HRP | Signal with enhancer | Signal without enhancer | Background with enhancer without HRP |
| | IMP | | | | | | | | |
| 1. | 713 | 0 | 0 | 87,085 | 3309 | 0 | 153,538 | 19,669 | 3 |
| 2. | 606 | | | 123,493 | | | 300,626 | | |

TABLE 3-continued

| | Light output, mV/second, integrated over the preceding one minute | | | | | | | | |
|---|---|---|---|---|---|---|---|---|---|
| | pH 6.5 | | | pH 8.1 | | | pH 8.8 | | |
| Time (mins.) | Signal with enhancer | Signal without enhancer | Background with enhancer without HRP | Signal with enhancer | Signal without enhancer | Background with enhancer without HRP | Signal with enhancer | Signal without enhancer | Background with enhancer without HRP |
| 5. | 153 | | | 145,302 | | | 432,580 | | |
| | PIP | | | | | | | | |
| 1. | 2713 | 0 | 0 | 551,961 | 1851 | 346 | 337,442 | 18,019 | 265 |
| 2. | 2863 | | | 599,992 | | | 489,666 | | |
| 5. | 1057 | | | 379,373 | | | 491,353 | | |

EXAMPLE 4

This Example illustrates the use of ortho-benzimidazol-2-ylphenol (OBIMP), otherwise known as 2-(2hydroxyphenyl)benzimidazole, as an enhancer of chemiluminescent reactions.

The procedure of Example 1 was repeated using as the enhancer OBIMP prepared as described by D. W. Hein et al., J. Amer. Chem. Soc. 79, 427–429 (1957). The product, m.p. 240° C., U. V. λ max 321 (Hein et al quote m.p. 242° C., λ max. 319), was dissolved at 1 mg./ml and 0.1 mg./ml DMSO. No enhancement was obtained and the signal: background ratio was between 1:1 and 2:1. However, by doubling the amount of oxidant used, to 100 microliters of the solution, the signal integrated over the first minute was 1456 mV/sec. compared with values of 4 in the absence of enhancer and 480 in the absence of HRP. When the enhancer was present and luminol was omitted a zero signal was obtained.

It is expected that the signal: background ratio would be improved when the OBIMP is further purified.

We claim:

1. In a method of enhancing the light output from a chemiluminescent reaction of a dihydrophthalazinedione (DPD), a peroxidase enzyme catalyst and an oxidant, in the presence of a phenolic compound as enhancer, wherein the improvement comprises utilizing as the enhancer a phenol substituted at its ortho and/or para position by an imidazolyl or benzimidazolyl group.

2. In a method of luminescent or luminometric assay which comprises carrying out a chemiluminescent reaction between a peroxidase, an oxidant and a chemiluminescent 2,3-dihydro-1,4-phthalazinedione (DPD), in the presence of a sensitivity-enhancing phenolic compound, and measuring or detecting the chemiluminescence thereby produced, wherein the improvement comprises carrying out the reaction in the presence of a phenol substituted at its ortho and/or para position by an imidazolyl or benzimidazolyl group.

3. In a method of diagnostic assay of a substance, the presence or amount of which is relatable to the presence or amount of a reaction partner selected from the group consisting of a dihydrophthalazinedione (DPD), a peroxidase enzyme and an oxidant, and a phenolic compound as enhancer of the sensitivity of the assay, which together are reactable in a chemiluminescent reaction, wherein said reaction is carried out, the light output thereof is detected or measured and thence the presence or amount of the substance to be assayed is related thereto, wherein the improvement comprises utilizing as the phenolic compound enhancer a comprises phenol substituted at its ortho position, para position or both said positions, by an imidazolyl or benzimidazolyl group.

4. A method according to claim 1, 2 or 3 wherein the phenolic compound is p-imidazol-1-ylphenol of formula:

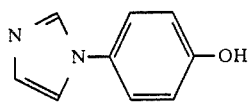

or o-benzimidazol-2-ylphenol of formula:

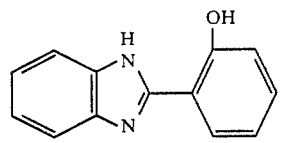

5. A method according to claim 2 or 3 wherein the peroxidase enzyme is free or conjugated to a ligand and the presence or amount of the peroxidase is determined from the presence or amount of light output.

6. A method according to claim 1, 2 or 3 wherein the peroxidase is horseradish peroxidase.

7. A method according to claim 1, 2 or 3 wherein the oxidant is hydrogen peroxide.

8. A method according to claim 1, 2 or 3 wherein the DPD is luminol.

9. A method according to claim 1 wherein the chemiluminescent reaction is carried out at a pH of from 7.5 to 9.

10. In a kit for use in diagnostic assay comprising in separate containers:
 a chemiluminescent dihydrophthalazinedione (DPD);
 a peroxidase enzyme catalyst; and
 a peroxidase enzyme catalyst; and
 a phenolic compound enhancer,
wherein the improvement comprises utilizing as said enhancer a phenol substituted at its ortho and/or para position by an imidazolyl or benzimidazolyl group.

11. A kit according to claim 10 wherein the phenolic compound is p-imidazol-1-ylphenol of formula:

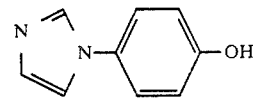

or o-benzimidazol-2-ylphenol of formula:

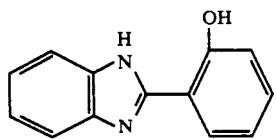
12. A kit according to claim 10 or 11 wherein the peroxidase is conjugated to a ligand.
13. A kit according to claim 10 or 11 wherein the peroxidase is horseradish peroxidase.
14. A kit according to claim 10 or 11 which further comprises an oxidant.
15. A kit according to claim 10 or 11 which further comprises hydrogen peroxide.
16. A kit according to claim 10 or 11 wherein the DPD is luminol.
* * * * *